United States Patent [19]

Bison et al.

[11] Patent Number: 4,791,210

[45] Date of Patent: Dec. 13, 1988

[54] PROCESS FOR THE PRODUCTION OF 5-METHYLTETRAZOLE

[75] Inventors: Günter Bison, Troisdorf; Johannes Schlupp, Bergisch-Gladbach; Josef Winterscheid, St. Augustin; Klaus Thewalt, Witten, all of Fed. Rep. of Germany

[73] Assignee: Dynamit Nobel Aktiengesellschaft, Troisdorf, Fed. Rep. of Germany

[21] Appl. No.: 106,872

[22] Filed: Oct. 13, 1987

[30] Foreign Application Priority Data

Oct. 11, 1986 [DE] Fed. Rep. of Germany ....... 3634717

[51] Int. Cl.$^4$ ............................................. C07D 257/04
[52] U.S. Cl. .................................................... 548/250
[58] Field of Search ......................................... 548/250

[56] References Cited

PUBLICATIONS

Buchanan et al. J. of Med. Chem. 12 (1969) pp. 1001 and 1002.

Primary Examiner—Glennon H. Hollrah
Assistant Examiner—D. B. Springer
Attorney, Agent, or Firm—Antonelli, Terry & Wands

[57] ABSTRACT

5-Methyltetrazole can be produced by reacting acetonitrile with an alkali azide or ammonium azide in high purity and a yield of above 98% by using a trialkyl amine as the solvent or suspension agent and by using the associated hydrochloride of the amine as the catalyst.

8 Claims, No Drawings

PROCESS FOR THE PRODUCTION OF 5-METHYLTETRAZOLE

This invention relates to a process for the industrial production of 5-methyltetrazole of the formula:

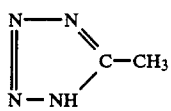

5-Methyltetrazole serves as a pharmaceutical intermediate, especially as a basis for the preparation of antibiotics.

According to the state of the art, the production of 5-methyltetrzazole from acetonitrile, thioacetamide, acetamidrazone hydrochloride or 1-ethoxy-1,1-diazidoethane is conventional. These known manufacturing methods have the drawbacks of unsatisfactory yields, in part difficult to obtain starting materials, and a hazardous reaction when using hydrazoic acid. On account of inadequate yields, the formation of by-products occurs and these by-products are prone to decomposition and are dangerous. The and the by-products can be removed only with difficulties and at great expense.

The production of 5-methyltetrazole by treating acetonitrile with hydrazoic acid proceeds slowly and results in yields of merely about 50%. According to German Pat. No.962,798, 5-methyltetrazole can be obtained from thioacetamide—in place of the low-reactivity acetonitrile in this reaction scheme—in tetrahydrofuran as a solvent by reaction with aluminum azide in a total yield of 63%. However, this use of aluminum azide in place of sodium azide is expensive since only one of three bound azide ions is utilized for the reaction.

Finnegan, et al. (J. Am. Chem. Soc. 80: 3908 [1958]) report that in the synthesis of 5-substituted tetrazoles by reaction of an organic nitrile with an azide in dimethylformamide or dimethyl sulfoxide in the presence of a catalyst, higher yields are obtained than when using other solvents. Among the catalysts are, for example, ammonium chloride. However, ammonium chloride leads to the formation of ammonium azide forming a readily decomposable sublimate at cold locations, for example, on a cooler. Finnegan does not use free amines.

According to DOS No. 2,809,798 an attempt is made to overcome these disadvantages in the production of 5-substituted tetrazoles by reacting a nitrile with an alkali azide or ammonium azide in the presence of monoalkyl amines or dialkyl amines in the presence of the associated acid addition salts of the amine. However, yields of 60–70% are attained only with the system of morpholine/morpholine . HCl. When utilizing this method for the production of 5-methyltetrazole, the product (see comparative example) is obtained in an only low yield. The formation of secondary products requires expensive purification operations so that the process is cumbersome and uneconomical.

Accordingly, there is a need for an economical industrial process for manufacturing 5-methyltetarazole without hazards and in high yields. The invention, therefore, is dedicated to solving this problem.

It has now been discovered that, with the use of, in particular, triethylamine as the diluent, suspension agent, or solvent, and in the presence of triethylamine hydrochloride as a catalyst, 5-methyltetrazole is obtained, surprisingly, when reacting acetonitrile with an alkali azide or optionally ammonium azide, in the very high yield of above 95% and in purities of more than 98%. Yields of far above 99% and purities of like magnitude are attainable. In general, it is possible to use trialkyl amines and the associated hydrochlorides of the, respectively, employed amines with alkyl groups having chain lengths of $C_1$ to $C_4$, among which triethylamine is highly preferred and tripropylamine is preferred. It is very much preferred to operate in the absence of additional solvents. Advantageously in the process of the present invention, it is no longer necessary to perform cumbersome purification operations.

The process, on account of an only minor excess pressure buildup of about 3 bar, can be conducted at reaction temperatures of about 105°–115° C. in the usually available agitator-equipped reactors so that no special pressure vessels are required. Suitable amines are, in this case, especially triethylamine and optionally tripropyleamine.

Reaction temperatures of 90°–160° C. are suitable; 110°–135° C. is preferred. The reactants are used in an equimolar ratio or preferably with an excess of the azide of 0.02–15 and, very preferably, 2.0–12 mol-%. The hydrochloride can be utilized in an equimolar quantity or in an excess of 0.02–10 mol-%, based on the azide.

The alkali salt of 5-methyltetrazole, initially formed when the trialkyl amine is removed in the presence of alkali hydroxide, is almost entirely devoid of by-products. Liberation of 5-methyltetrazole with hydrochloric acid thus takes place without encountering the previous hazards due to by-products and their decomposition. The product can be passed on to its use in crystalline form or in a solution with organic solvents.

The following examples and comparative example further illustrate the advantages of the process of this invention.

COMPARATIVE EXAMPLE ACCORDING TO DOS NO. 2,809,798

Acetonitrile: 20.5 g (0.5 mol),
morpholine hydrochloride: 67.9 g (0.55 mol),
sodium azide: 35.8 g (0.55 mol)
were suspended in 332 ml of morpholine and heated for 13 hours to 130° C. After cooling of the reaction mixture to 15° C., 28.7 g=89.3% of the thus-separated sodium chloride was removed. The dark-colored reaction solution was concentrated with the aid of a water-jet aspirator, the residue was taken up in water, the pH was raised to a pH of 13 with 10% by weight sodium hydroxide solution. Subsequently, the solution was clarified with filtering aids and concentrated. This purification step of taking up the residue in water and clarifying with activated carbon was repeated twice. The presently remaining residue was extracted with acetone in a Soxhlet apparatus, then the acetone was removed in a rotary evaporator, and the resultant product was recrystallized from n-butyl acetate. Yield based on acetonitrile employed: 60% of theory

EXAMPLE 1

20.5 g (0.5 mol) of acetonitrile,
75.7 g (0.55 mol) of triethylamine hydrochloride
35.8 g (0.55 mol) of sodium azide were suspended in 418 ml of triethylamine in an agitated autoclave having a capacity of one liter, and the mixture was heated for 6 hours to 130° C.

After cooling, the triethylamine was extensively removed at 50° C. by distillation with the aid of a water-jet aspirator. The distillation residue was dissolved in water, brought to pH 12.8 with NaOH (10% by weight), and triethylamine and water were removed by a water-jet aspirator. The colored residue was dissolved in 250 ml of water, brought to pH 1.2 with concentrated hydrochloric acid, and the solution was clarified with active carbon. The solution was dehydrated azeotropically with isobutanol, and thus-separated sodium chloride was removed After removal of isobutanol by distillation, 41.9 g of a crystalline product was obtained, i.e. 5-methyltetrazole mp 139°-142° C. (98% purity). Yield, based on acetonitrile employed: 98.1% of theory

EXAMPLE 2

An enamelled agitated vessel having a capacity of 800 l was charged with
20.5 kg (0.50 kmol) of acetonitrile,
75.0 kg (0.59 kmol) of triethylamine hydrochloride
35.8 kg (0.55 kmol) of sodium azide in
305 kg of triethylamine,
and the mixture was heated for 6 hours at 115° C., resulting in a pressure of 4 bar within the reactor. After cooling to 20° C. and expansion of the reactor, two layers had been formed. The triethylamine layer was separated. The layer containing the product was combined with 100 l of water and the suspension was adjusted to pH 12.9 with 10% by weight sodium hydroxide solution. The thus-released triethylamine was distilled off by means of a water-jet aspirator, the residue was combined with 100 l of water and brought to pH 1.3 with concentrated HCl. The solution was clarified with activated carbon whereupon water was distilled off and residual proportions were removed azeotropically with isobutanol. Sodium chloride that had separated from this solution was removed therefrom by means of a forced-suction filter, and the product was isolated as in Example 1.

Yield: 42.4 kg of the product 5-methyltetrazole (mp 139°-142° C.) having a purity of 98.7%, 99.8% of theory.

EXAMPLE 3

Example 1 was repeated, but using 0.55 mol of tripropylamine HCl an 400 ml of tripropylamine. Yield and purity of the product correspond to those in Example 1.

EXAMPLE 4

Example 1 was repeated, but using 0.53 mol of ammonium azide and a reaction temperature of 120° C. Yield and purity of the product correspond to those in Example 1.

What is claimed is:

1. A process for the production of 5-methyltetrazole of the formula:

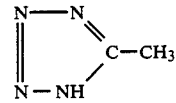

which comprises reacting acetonitrile with an ammonium or alkali azide at reaction temperatures of 90°-160° C. in the presence of a trialkylamine solvent and an HCl addition salt thereof as a catalyst, said trialkylamine having alkyl groups containing 1 to 4 carbon atoms and said salt catalyst being a hydrochloride of a trialkylamine having alkyl groups containing 2 to 4 carbon atoms; the salt catalyst being present in equimolar quantity or in an excess of 0.02-10 mol-%, based on the azide.

2. A process according to claim 1, wherein the reaction of the acetonitrile and the azide is conducted at reaction temperatures of 110°-135° C.

3. A process according to claim 1, wherein the acetonitrile and the azide are employed in an equimolar ratio.

4. A process according to claim 1, wherein the ammonium or alkali azide is employed in a molar excess of 0.02-15 mol-%.

5. A process according to claim 1, wherein the ammonium or alkali azide is employed in a molar excess of 2-12 mol-%.

6. A process according to claim 1, wherein the trialkyl amine hydrochloride is employed in a molar excess of 0.02-10 mol-%, based on the azide.

7. A process according to claim 1, wherein the trialkylamine is triethylamine and the salt is triethylamine hydrochloride and acetronitrile is reacted with sodium azide.

8. A process according to claim 1, wherein the acetonitrile is reacted with ammonium azide.

* * * * *